United States Patent [19]

Liu

[11] Patent Number: 4,634,765

[45] Date of Patent: Jan. 6, 1987

[54] HOMODISACCHARIDE HYPOGLYCEMIC AGENTS

[75] Inventor: Paul S. Liu, Indianapolis, Ind.

[73] Assignee: Merrell Dow Pharmaceuticals Inc., Cincinnati, Ohio

[21] Appl. No.: 683,127

[22] Filed: Dec. 18, 1984

[51] Int. Cl.$^4$ ............................................. C07H 17/02
[52] U.S. Cl. .................................... 536/17.4; 536/17.9
[58] Field of Search ...................... 536/17.2, 4.1, 17.9, 536/17.4; 514/23

[56] References Cited

U.S. PATENT DOCUMENTS

| | | | |
|---|---|---|---|
| 4,065,562 | 12/1977 | Ohata et al. | 424/267 |
| 4,260,622 | 4/1981 | Junge et al. | 424/267 |
| 4,328,233 | 5/1982 | Boshagen et al. | 424/267 |
| 4,348,402 | 9/1982 | Kinast et al. | 536/17.2 |
| 4,465,671 | 8/1984 | Angelucci et al. | 536/6.4 |

OTHER PUBLICATIONS

Liu, abstracts of papers, 187th ACS National Meeting, St. Louis, Missouri (1984), CARB 33.

Primary Examiner—Johnnie R. Brown
Assistant Examiner—Elli Peselev
Attorney, Agent, or Firm—John J. Kolano

[57] ABSTRACT

Homonojirimycin glycosides active as inhibitors of carbohydrate digestive enzymes are described herein. The compounds are prepared by the reaction of an appropriately protected homonojirimycin with a protected glycosyl halide followed by removal of the protecting groups.

7 Claims, No Drawings

HOMODISACCHARIDE HYPOGLYCEMIC AGENTS

The present invention is directed to homonojirimycin glycosides which show activity as inhibitors of carbohydrate digestive enzymes and would thus be useful as antidiabetic agents. Systematically, homonojirimycin is named 2,6-imino-2,6-dideoxy-D-glycero-L-gulo-heptitol. Specifically, the present invention is directed to compounds having the following general formula:

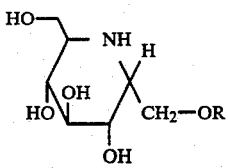

wherein R is a glycosyl or acylated glycosyl radical. The glycosyl radicals contain from 1 to 3 hexose or pentose units and attachment is at the 1-position of the glycosyl radical. Acid addition salts of the aforesaid compounds with pharmaceutically acceptable acids are also part of the present invention.

In the acylated glycosyl radicals referred to above, any hydroxy groups are esterified with an alkanoic acid containing up to 6 carbon atoms or benzoic acid. Acetyl esters are preferred esters. Specific examples of glycosyl radicals are glucosyl, galactosyl, fucosyl, ribosyl, cellobiosyl, maltobiosyl, maltotriosyl, cellotriosyl, arabinosyl and xylosyl. Particularly preferred are the compounds wherein R is 1-glucosyl, 1-L-fucosyl or 1-cellobiosyl.

Acid addition salts with pharmaceutically acceptable acids referred to above are equivalent to the amines for the purpose of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid.

The compounds of the present invention are prepared by the reaction of 2,6-benzyloxycarbonylimino-2,6-dideoxy-1,3,4,5,-tetrakis-O-(phenylmethyl)-D-glycero-L-gulo-heptitol with an appropriately protected glycosyl bromide or chloride. By appropriately protected glycosyl is meant a glycosyl wherein any free hydroxy group is protected as an ester or with a benzyl group. Preferred esters are the acetate ester or the benzoate ester althought other alkanoyl esters, particularly those containing up to six carbon atoms, can be used. The reaction is carried out at room temperature in an inert solvent such as methylene chloride in the presence of a mercuric salt and a appropriate molecular sieve. Mercuric bromide and mercuric cyanide are preferred mercuric salts and they are used in catalytic amounts. The molcular sieve acts as a drying agent and as a weak base to pick up acid.

The procedure described above gives a product in which all the hydroxy groups and the amino group are still protected and it is necessary to remove these protecting groups to obtain the desired product having free hydroxy and amino groups. This is most readily done using standard debenzylation techniques with catalytic hydrogenation in an appropriate solvent such as ethanol and with a catalyst such as Pd/C. Where all of the protecting groups are the same and are benzyl, this procedure would give a product with all of the hydroxy groups free. On the other hand, if an esterified glycosyl halide had been used, the above procedure would give a product in which the glycosyl hydroxys were still protected as esters and this would provide an appropriate method for obtaining such esterified compounds.

If esterified glycosyl halides are used as starting materials in the above procedure but completely hydroxylated products are desired then the coupling product as described earlier is treated with sodium methoxide in methanol to hydrolyze the esters and then debenzylated using hydrogenation and a Pd/C catalyst as described earlier.

The catalytic debenzylation referred to above is usually carried out in the presence of an acid (pharmaceutically acceptable) so that the product is obtained in the form of the corresponding salt. The salt can be converted to the coresponding free base by passage through an appropriate ion exchange column or by other standard neutralization procedures. The resultant free amine can then be reacted with another acid by standard procedures to give the corresponding salt.

The 2,6-(benzyloxycarbonylimino)-2,6-dideoxy-1,3,4,5,-tetrakis-O-(phenylmethyl)-D-glycero-L-gulo-heptitol starting material referred to above can be obtained by starting from 2,3,4,6-tetra-O-(phenylmethyl)-D-glucopyranose. The glucopyranose is reacted with mehtylenetriphenylphosphorane in a Wittig reaction to give the corresponding methylene compound as described by Pougny et al., *J. Chem. Soc., Chem. Comm.*, 375 (1981). The free hydroxy group then present in the molecule is oxidized to the corresponding ketone which is then converted to the oxime. The oxime is reduced to the corresponding amine using a metal hydride reducing agent such as lithium aluminum hydride or bis(2-methoxyethoxy)aluminum hydride in benzene and the amine is then reacted with benzyloxycarbonyl chloride according to standard procedures to give the corresponding carbamate.

The unsaturated carbamate can then be cyclized to the desired piperidine by first using mercuric acetate or mercuric trifloroacetate in an inert slovent such as tetrahydrofuran to give an organo-mercury compound followed by aqueous potassium chloride and then sodium borohydride and oxygen. Preferably, however, the unsaturated carbamate is treated with mercuric acetate followed by aqueous potassium chloride and then iodine in acetic acid to give a cyclic carbamate (five-membered ring). The carbamate is then hydrolyzed using potassium hydroxide in aqueous ethanol and the resulting product is then treated with benzyloxycarbonyl chloride to give the desired reactant for the final coupling step.

Compounds involved in the conversion of 2,3,4,6,-tetra-O-(phenylmethyl)-D-glucopyranose to 2,6-(benzyloxycarbonylimino)-2,6-dideoxy-1,3,4,5-tetrakis-O-(phenylmethl)-D-glycero-L-gulo-heptitol (via the cyclic carbamate) are shown below. In the structural formulas, Bn is phenylmethyl and CBZ is benzyloxycarbonyl.

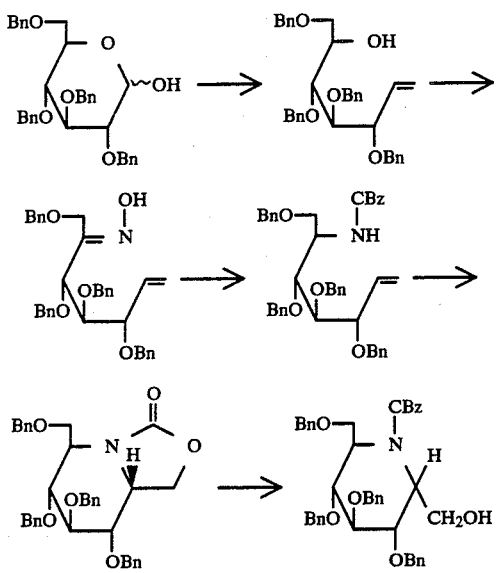

The present compounds are useful in the treatment of diabetes. More specifically, they can be used to prevent the development of hyperglycemia which may be observed in certain diabetic conditions when a glucose precursor is ingested. Rather than achieving this effect by promoting the metabolism of glucose present in the blood, the present compounds act by preventing the initial formation of glucose in the body thereby holding down the quantity of glucose which could eventually appear in the blood.

The mechanism whereby this result is achieved is the following although the utility described above should not be limited by the precise details of this mechanism. Enzymes which catalyze the hydrolysis of complex carbohydrates convert non-absorbable carbohydrate into absorbable sugars. The rapid action of these enzymes lead to acute and undesirable elevations in blood glucose in diabetes. The compounds of the present invention are potent inhibitors of these enzymes and, when co-administered with a carbohydrate meal, they prevent harmful hyperglycemic excursions of this type. It is desirable, however, that the inhibition of these hydrolytic enzymes be limited to those present in the intestines and that is true for the present compounds. Otherwise, inhibition of systemic glycohydrolases or glucose transport can lead to difficulty in the utilization of intracellular carbohydrates as an energy-source and thus cause metabolic problems.

The following test procedures can be used to demonstrate the activity of the present compounds. Compound I is 2,6-imino-2,6-dideoxy-7-O-($\beta$-D-glucopyranosyl)-D-glycero-L-gulo-heptitol hydrochloride dihydrate and Compound II is 2,6-imino-2,6-dideoxy-7O-($\alpha$-D-glucopyranosyl)-D-glycero-L-gulo-heptitol hydrochloride dihydrate.

Starch Load

ICR-Swiss mice, fasted for 18–20 hours, were dosed p.o. with the compound and this was followed 15 minutes later by a methocel suspension of starch at 1 g/kg p.o. At 45 minutes post starch, the animals were sacrificed and their blood glucose was determined. The drug's ability to inhibit the blood glucose elevation was calculated as a percentage from the blood glucose of animals dosed only with starch (Starch Control) to the blood glucose of undosed fasting animals (Fasting Control). This value is noted as Serum glucose Lowering (SGL).

| SGL WITH COMPOUND | | |
|---|---|---|
| Dose (mg/kg) | Compound I | Compound II |
| 5 | 8% | 40% |
| 10 | 12% | 23% |
| 20 | 52%* | 79%* |
| 40 | 63%* | 51%* |

*Significant (Student's t-test) P $\leq$ 0.05

Sucrose Load

Experimental parameters are identical to the starch load study except that the mice were sacrificed 30 minutes after an oral sucrose load of 2 g/kg.

| SERUM GLUCOSE LOWERING (%) | | |
|---|---|---|
| Dose (mg/kg) | Compound I | Compound II |
| 5 | 58%* | 80%* |
| 10 | 93%* | 73%* |
| 20 | 94%* | 107%* |
| 40 | 106%* | 91%* |

*Significant (Student's t-test) p $\leq$ 0.05

Glucose Load

Experimental parameters are identical to the starch load study except that the mice were sacrificed 10 minutes after an oral glucose load of 0.5 g/kg. The dose of the test compounds was increased to 100 mg/kg, p.o.

| SERUM GLUCOSE LOWERING (%) | | |
|---|---|---|
| Dose (mg/kg) | Compound I | Compound II |
| 100 | 2% | 5% |

The oral dose of 100 mg/kg that was 20 fold greater than the lowest dose that decreased the blood glucose concentration arising from a 2 g/kg sucrose load had no effect on intestinal glucose transport.

The compounds did not show any toxicity at 200 mg/kg (i.p. and p.o.) in mice.

In praticing the method of this invention, an amount of one of the compounds effective to inhibit postprandial hyperglycemia is adminstered to a mammal in need thereof by a suitable route. For the purposes of this invention, oral adminstration is preferred.

The effective amount of the compound, that is, the amount sufficient to inhibit postprandial hyperglycemia, depends on various factors such as the size, type and age of the animal to be treated, the particular compound or pharmaceutically acceptable salt employed, the frequency of administration, the severity of the condition and the time of administration. Generally speaking, the compounds would be administered orally at a dose of 0.5 mpk to 50 mpk, with a dose of 1.5 mpk to 15 mpk being preferred. More specifically, the present compounds would be adminstered to human in single unit doses containing 100 mg to 1 g of active ingredient with the material being administered three times a day at mealtime.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal adminstration to animals, and which are substantially non-toxic and non-sensitizing under conditions of use. The compositions can be prepared by known techniques for the preparation of tablet, capsules, elixirs, syrups emulsions, dispersions and wettable and effervescent powders, and can contain suitable excipients known to be useful in the preparation of the particular type of composition desired. Suitable pharmaceutical carriers and formulation techniques are found in standard texts, such as *Remington's Pharmaceutical Sciences*, Mack Publishing Company, Easton, Pa.

The following examples are presented to illustrate the present invention. However, they should not be construed as limiting it in any way.

EXAMPLE 1

2,3,4,6,-Tetra-O-(phenylmethyl)-D-glucopyranose was converted to 1,2-didehydro-1,2dideoxy-3,4,5,7-tetrakis-O-(phenylmethyl)-D-glucoheptitol using the Wittig reagent according to the procedure of Pougny, et al., *J. Chem. Soc., Chem. Commun.*, 375 (1981).

To a stirred solution of 50 g of this heptitol in 180 ml of toluene was added 45 g of dicyclohexylcarbodiimide, 25 ml of dimethyl sulfoxide and 10 ml of pyridine. This was followed by the dropwise addition of 10 ml of trifluoroacetic acid. The resulting mixture was stirred at room temperature for 3 hours and then 50 ml of water was added followed by 250 ml of ether. The resulting cloudy mixture was filtered through Celite and the aqueous layer was separated and extracted twice with 100-ml portions of ether. The organic solutions were combined and washed successively with 1 N hydrochloric acid (two 200-ml portions), saturated sodium bicarbonate solution (500 ml) and brine (500 ml). The organic layer was dried over anhydrous magnesium sulfate and the solvent was evaporated in vacuo to give a crude yellow syrupy material which is 6,7-didehydro-6,7dideoxy-1,3,4,5-tetrakis-O-(phenylmethyl)-D-xyloheptos-2-ulose.

EXAMPLE 2

To a stirred solution of 46 g of 6,7-didehydro-6,7-dideoxy-1,3,4,5-tetrakis-O-(phenylmethyl)-D-xyloheptos-2-ulose in 400 ml of methanol was added 35 g of potassium bicarbonate and 25 g of hydroxylamine hydrochloride and the mixture was heated under reflux for 30 minutes. It was then cooled and filtered, the solvent was evaporated from the filtrate in vacuo, and the resulting residue was redissolved in ether. The ether solution was washed successively with 1 N hydrochloric acid, saturated aqueous sodium bicarbonate solution, and aqueous sodium chloride solution and then dried over magnesium sulfate. Evaporation of the solvent gave a golden syrup which was purified using flash chromatography to give a colorless oily product which was a inseparable mixture of the syn- and anti- oximes of 6,7-didehydro-6,7dideoxy-1,3,4,5-tetrakis-O-(phenylmethyl)-D-xyloheptos-2-ulose (TLC, 1:4 ethyl acetate-hexane, silica gel, $R_f=0.24$).

EXAMPLE 3

A solution of 31 g of the oxime obtained in the preceding example in 150 ml of dry ether was added dropwise to a stirred suspension of 3.8 g of lithium aluminum hydride in 150 ml of ether. The mixture was stirred for an addition 2 hours at room temperature after the addition was complete. Ethyl acetate (90 ml) was then added slowly to decompose the excess lithium aluminum hydride and this was followed by the addition of 30 ml of 5 N aqueous sodium hydroxide solution. The resulting cloudy suspension was filtered through a bed of Celite and the Celite cake was washed thoroughly with ether. The filtrate and washings were combined and extracted with saturated aqueous sodium bicarbonate solution and brine and then dried over magnesium sulfate. Evaporation of the solvent from the organic solutions gave a crude syrupy amine product. This crude product was dissolved immediately in 150 ml of tetrahydrofuran and then 20 g of anhydrous potassium carbonate was added. The resulting slurry was stirred under nitrogen and then a solution of 7 ml of benzyl chloroformate in 20 ml of tetrahydrofuran was added and the mixture was stirred at room temperature for 1 hour. Water (50 ml) was then added and stirring was continued for an additional hour. The resulting mixture was poured into 300 ml of water and the resulting emulsion was extracted with two 500-ml portions of ether. The combined ether extracts were washed with saturated aqueous sodium bicarbonate solution, and brine and then dried over sodium sulfate. Concentration of the organic solution in vacuo gave a syrup which was shown to be a 1:6 mixture of two components by thin layer chromatography (1:4 ethyl acetate-hexane, silica gel, $R_f=0.50$ and 0.47 respectively). The major compound ($R_f=0.47$) was obtained by preparative HPLC as a colorless syrup. This product was 1,2-didehydro-1,2,6-trideoxy-6-[[(phenylethoxy)carbonyl amino]-3,4,5,7-tetrakis-O-(phenylmethyl)-D-glucoheptitol.

EXAMPLE 4

To a solution of 21 g of the carbamate product obtained in Example 3 in 300 ml of dry tetrahydrofuran there was added 20 g of mercuric acetate and the mixture was stirred at 50° C. under nitrogen for 16 hours. The solvent was evaporated from the mixture under reduced pressure and the residue was redissolved in 500 ml of chloroform. The chloroform solution was mixed thoroughly with 250 ml of saturated aqueous potassium chloride solution. The organic layer was then dried over magnesium sulfate and evaporation of the solvent in vacuo gave a syrup which was dissolved in 100 ml of dimthylformamide and added dropwise to a stirred suspension of 2.2 g of sodium borohydride in 80 ml of dimethylformamide with continuous infusion of oxygen. After the addition was complete, the mixture was stirred for 1 hour and then diluted with 300 ml of ether. The resulting suspension was filtered through a bed of Celite and the filtrate was added to water and mixed thoroughly. The layers were separated and the aqueous portion was extracted with ether. The combined ether extracts were washed with saturated aqueous sodium bicarbonate solution and brine and dried over magnesium sulfate. The residue resulting from evaporation of the solvent was dissolved in 50 ml of ether and kept at 4° C. for 16 hours. The cooled solution was filtered and concentrated in vacuo to provide a syrupy residue which was 2,6-dideoxy-2,6-[[(phenylmethoxy)carbonyl]imino]-1,3,4,5-tetrakis-O-(phenylmethyl)-D-glycero-L-gulo-heptitol.

EXAMPLE 5

A slurry of 6.2 g of 2,6-dideoxy-2,6-[[(phenylmethoxy)carbonyl]imino]-1,3,4,5-tetrakis-O-(phenylmethyl)-D-glycero-L-gulo-heptitol, 4.8 g of mercuric bromide and 30 g of pulverized 4A molecular sieve in 100 ml of dry methylene chloride was stirred vigorously at room temperature for 1 hour. A solution of 16.2 mmol of 2,3,4,6-tetra-O-(phenylmethyl)-α-D-glucopyranosyl bromide [prepared according to the procedure of Ishikawa, et al., *J. Org. Chem.*, 34, 563 (1969)] in 20 ml of dry methylene chloride was added slowly to the slurry and the resulting mixture was stirred 16 hours at room temperature. The mixture was filtered and the filtrate was washed with saturated aqueous sodium bicarbonate and with brine and then dried over magnesium sulfate. Evaporation of the solvent gave a residual syrup which was chromatographed using preparative HPLC (elution solvent, 1:5 ethyl acetate-hexane) and fractions containing material with $R_f$=0.33 and 0.29 on TLC (elution solvent, 1:4 ethyl acetate-hexane, silica gel) were collected. Concentration of the individual eluates gave, a residues, golden syrups having the indicated $R_f$. The products thus obtained were, respectively, 2,6-dideoxy-2,6-[[(phenylmethoxy)carbonyl]imino]-7-O-[2,3,4,6-tetrakis-O-(phenylmethyl)-βD-glucopyranosyl]-3,4,5,7-tetrakis-O-(phenylmethyl)-D-glycero-L-gylo-heptitol and the corresponding α-D-glucopyranosyl compound.

EXAMPLE 6

A solution of 2.2 g of the first syrup referred to in Example 5 was dissolved in a mixture of 10 ml of chloroform, 40 ml of ethanol and 0.6 ml of 5 N hydrochloric acid. Catalyst (0.5 g of 10% Pd/C) was added and the mixture was hydrogenated in a Parr apparatus (P=4.6 atm) for 3 days. The mixture was then filtered and the filtrate was concentrated under reduced pressure to give a hygroscopic solid which was 2,6-imino-2,6-dideoxy-7-O-(β-D-glucopyranosyl)-D-glycero-L-gulo-heptitol hydrochloride melting at about 131°–134° C. The free base of this compound has the following structural formula:

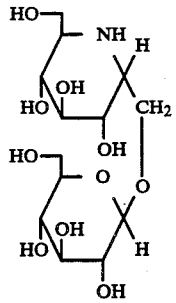

When the above procedure was repeated using the second product obtained in Example 5, the resulting product was 2,6-imino-2,6-dideoxy-1-(α-D-glucopyranosyl)-D-glycero-L-gulo-heptitol hydrochloride dihydrate melting at about 125°–128° C.

EXAMPLE 7

To a solution of 3.2 g of the isomeric mixture of carbamates obtained in Example 3 in 25 ml of dry tetrahydrofuran was added 1.67 of mercuric acetate and the mixture was stirred under nitrogen at 55° C. for 16 hours. The resulting mixture was then cooled and the solvent evaporated in vacuo and the reside was dissolved in 40 ml of methylene chloride. The methylene choride extract was then shaken thoroughly 30 ml of aqueous saturated potassium chloride solution. The organic extract was then dried over magnesium sulfate and the solvent evaporated to give 4.1 g of a mercuric complex. The syrupy complex was dissolved in 25 ml of glacial acetic acid and 1.25 g of iodine was added in portions to the solution. The dark mixture was then stirred at room temperature for 16 hours. The red mercuric salts which precipitated were filtered with the aid of Celite and the filter pad was washed with ethyl acetate (80 ml). The filtrate and washings were combined and mixed thoroughly with aqueous saturated sodium thiosulfate solution (2×100 ml). The organic extract was then cooled and stirred with an ice cold solution of aqueous 2 N sodium hydroxide (250 ml) for 30 minutes. The organic layer was washed with brine and with saturated aqueous sodium bicarbonate solution, with brine again and it was finally dried over magnesium sulfate. Evaportion of the solvent gave a syrupy residue which was readily purified by flash chromatography (silical gel, elution solvent 1:2 ethyl acetatehexane). The major product was fractionally crystallized from ether/petroleum ether to give 2,6-(carboxyimino)-2,6-dideoxy-3,4,5,7-tetrakis-O-(phenylmethyl)-D-glycero-D-idoheptitol, intramol. 2,1-ester as colorless needle-shaped crystals melting at about 77°–79° C.

EXAMPLE 8

To a solution of 21.6 g of the product obtained in Example 7 in 200 ml of ethanol was added 20 ml of 50% (w/v) aqueous potassium hydroxide solution and the mixture was heated under reflux for 16 hours. The mixture was than cooled and diluted with 100 ml of water. After saturating the aqueous phase with sodium chloride, the mixture was extracted with two 400-ml portions of methylene chloride. The combined extracts were dried over sodium sulfate and the solvent evaporated to leave residual crude amine. This residual oily amine was dissolved in 200 ml of tetrahydrofuran and 15 g of potassium carbonate and 6 ml of benzyl chloroformate were added and the mixture was stirred vigorously at room temperature. After 30 minutes, 50 ml of water was added stirring was continued for an additional hour. The mixture was then diluted with 150 ml of ether and the two layers were separated. The organic layer was washed with saturated aqueous sodium bicarbonate solution and with brine and dried over magnesium sulfate. Evaporation of the solvent left a residual oil which was 2,6-dideoxy-2,6-[[(phenylmethoxy)carbonyl]imino]-1,3,4,5-tetrakis-O-(phenylmethyl)-D-glycero-L-gulo-heptitol.

EXAMPLE 9

To a solution of 24 g of the compound obtained in Example 8 in 320 ml of a 1:1 mixture of toluene and nitromethane was added 20 g of 2,3,4,6-tetracetyl-α-D-glucopyransosyl bromide, 12.3 g of mercuric cyanide and 24 g of molecular sieve 4A. The mixture was stirred under nitrogen and heated at 60° C. for 3–4 hours. The mixture was then cooled and diluted with 400 ml of ether and then 400 ml of saturated aqueous sodium bicarbonate solution was added. After stirring vigorously for 15 minutes, the two layers were separated and the organic layer was washed successively with saturated aqueous sodium thiosulfate solution, aqueous saturated sodium bicarbonate solution and brine. The mixture was then dried over magnesium sulfate and the solvent was evaporated to give a syrupy residue which was 2,6-dideoxy-2,6-[[(phenylmethoxy)carbonyl]imino]-7-O-(2,3,4,6-tetra-O-acetyl-β-D-glucopyranosyl)-1,3,4,5-tetrakis-O-(phenylmethyl)-D-glycero-L-glycero-L-gulo-heptitol.

EXAMPLE 10

To a solution of 28 g of the product obtained in Example 9 in 250 ml of methanol there was added 0.4 ml of a 25% sodium methoxide solution (methanol) and the mixture was stirred at room temperature for 16 hours. The solvent was then evaporated in vacuo to leave a residual thick syrup which was purified by flash chromatography (silica gel, elution sovent 9:1 ethyl acetate-hexane). Evaporation of the solvent from the combined fractions gave a dry foamy solid which was then hydrogenated in the usual manner over Pd/C catalyst in ethanol containing 1.2 equivalents of hydrochloric acid to give 2,6-imino-2,6-dideoxy-7-O-(β-D-glucopyranosyl)-D-glycero-L-gulo-heptitol hydrochloride dihydrate.

EXAMPLE 11

The procedures of Example 9 and 10 were repeated using 2,6-dideoxy-2,6-[[(phenylmethoxy)carbonyl]imino]-1,3,4,5-tetrakis-O-(phenylmethyl)-D-glycero-L-gulo-heptitol and the appropriate acetyl bromo sugar derivative. Where appropriate, the debenzylation was carried out in the presence of another acid in place of the hydrochloride acid to give the following compounds:

2,6-Imino-2,6-dideoxy-7-O(β-D-galactopyranosyl)-D-glycero-L-gulo-heptitol 4-methylbenzenesulfonate (salt) (1:1) melting at about 92°-97° C.

2,6-Imino-2,6-dideoxy-7-O(6-deoxy-β-L-galactopyranosyl)-D-glycero-L-gulo-heptitol 4-methylbenzenesulfonate (salt) (1:1) as a hygroscopic solid, ms=340 (MH+), 194 (BH+). In this case, the appropriate chloro sugar was used as the starting material instead of the bromo sugar.

2,6-Imino-2,6-dideoxy-7-O(6-deoxy-β-D-galactopyranosyl)-D-glycero-L-gulo-heptitol 4-methylbenzesulfonate (salt) (1:1) melting at greater than 90° C., ms=340 (MH+), 194 (BH+). In this case, the appropriate chloro sugar was used as the starting material instead of the bromo sugar.

2,6-Imino-2,6dideoxy-7-O-(β-D-ribofuranosyl)-D-glycero-L-gulo-heptitol hydrochloride as a hygroscopic solid, ms=326 (MH+), 308 (MH+-H₂O), 194 (BH+). In this case, a benzoyl sugar was used instead of the acetyl sugar.

O-α-D-Glucopyranosyl-(1→4)-O-β-D-glucopyranosyl-(1→7)-2,6-dideoxy-2,6-imino-D-glycero-L-gulo-heptitol 4-methylbenzenesulfonate (salt) melting at about 125°-145° C. (dec), ms=518 (MH+), 194 (BH+). O-2,3,4,6-Tetra-O-acetyl-O-α-D-glucopyranosyl-(1→4)-2,3,6-tri-O-acetyl-β-D-glucopyranosyl-(1→7)-2,6-dideoxy-2,6-[[(phenylmethoxy)-carbonyl]imino]-1,3,4,5-tetrakis-O-(phenylmethyl)-D-glycero-L-gulo-heptitol was an intermediate.

O-β-D-glucopyranosyl-(1→4)-O-β-D-glucopyranosyl-(1→7)-2,6-dideoxy-2,6-imino-D-glycero-L-gulo-heptitol 4-methylbenzenesulfonate (salt) melting at about 188°-190° C. (dec), ms=518 (MH+). O-2,3,4,6-Tetra-O-acetyl-O-β-D-glucopyranosyl-(1÷4)-2,3,6-tri-O-acetyl-O-β-D-glucopyranosyl-(1→7)-2,6-dideoxy-2,6-[[(phenylmethoxy)carbonyl]imino]-1,3,4,5tetrakis-O-(phenylmethyl)-D-glycero-L-gulo-heptitol was an intermediate.

EXAMPLE 12

If the product of Example 9 is directly hydrogenated as described in Example 10 without first hydrolyzing the ester groups, the product obtained is 2,6-imino-2,6-dideoxy-7-O-(2,3,4,6-tetra-O-acetyl-β-D-glucopyranosyl)-D-glycero-L-gulo-heptitol (hydrochloride).

What is claimed is:

1. A compound of the formula:

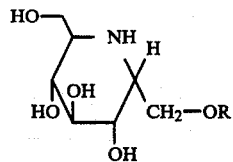

wherein R is a glycosyl or acylated glycosyl radical containing from 1 to 3 hexose or pentose units and attachment is at the 1-position of the glycosyl radical; and the pharmaceutically acceptable acid addition salts thereof.

2. A compound according to claim 1 having the formula:

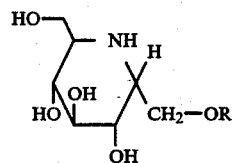

wherein R is glucosyl, galactosyl, fucosyl, ribosyl, cellobiosyl, maltobiosyl, maltotriosyl, cellotriosyl, arabinosyl and xylosyl.

3. A compound according to claim 1 having the formula:

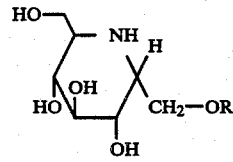

wherein R is 1-glucosyl, 1-L-fucosyl or 1-cellobiosyl.

4. A compound according to claim 1 which is 2,6-imino-2,6-dideoxy-7-O-(β-D-glucopyranosyl)-D-glycero-L-gulo-heptitol hydrochloride dihydrate.

5. A compound according to claim 1 which is 2,6-imino-2,6-dideoxy-7-O-(6-deoxy-β-D-galactopyranosyl)-D-glycero-L-gulo-heptitol 4-methylbenzenesulfonate salt.

6. A compound according to claim 1 which is 2,6-imino-2,6-dideoxy-7-O-(6-deoxy-β-L-galactopyranosyl)-D-glycero-L-gulo-heptitol 4-methylbenzenesulfonate salt.

7. A compound according to claim 1 which is O-β-D-glucopyranosyl-(1→4)-O-β-D-glucopyranosyl-(1→1)-2,6-dideoxy-2,6-imino-D-glycero-L-gulo-heptitol 4methylbenzenesulfonate salt.

* * * * *

UNITED STATES PATENT AND TRADEMARK OFFICE
CERTIFICATE OF CORRECTION

PATENT NO. : 4,634,765

DATED : January 6, 1987

INVENTOR(S) : Paul S. Liu

It is certified that error appears in the above-identified patent and that said Letters Patent are hereby corrected as shown below:

Column 1, line 61, "and a appropriate" should read -- and an appropriate --.
Column 2, line 35, "mehtylenetriphenylphosphorane" should read -- methylenetriphenylphosphorane --.
Column 2, line 49, "trifloroacetate" should read -- trifluoroacetate --.
Column 2, line 65, "(phenylmethl)" should read -- (phenylmethyl) --.
Column 3, line 57, "-7O-" should read -- -7-$\underline{O}$- --.
Column 5, line 23, "didehydro-1,2dideoxy" should read -- didehydro-1,2-dideoxy --.
Column 5, line 43, "6,7dideoxy" should read -- 6,7-dideoxy --.
Column 5, line 61, "was a inseparable" should read -- was an inseparable --.
Column 5, line 62, "-6,7dideoxy" should read -- -6,7-dideoxy --.
Column 6, line 35, "carbonyl amino]" should read -- carbonyl]amino] --.
Column 7, line 23, "a residues" should read -- as residues --.
Column 7, line 26, "-βD" should read -- -β-D --.
Column 7, line 27, "-3,4,5,7-" should read -- -1,3,4,5- --.
Column 7, line 60, "-dideoxy-1-" should read -- -dideoxy-7-$\underline{O}$- --.
Column 8, line 4, "shaken thoroughly 30 ml" should read -- shaken thoroughly with 30 ml --.
Column 9, line 34, "-7-O(β-" should read -- -7-$\underline{O}$-(β- --.
Column 9, line 37, "-7-O(6-" should read -- -7-$\underline{O}$-(6- --.
Column 9, line 43, "-7-O(6-" should read -- -7-$\underline{O}$-(6- --.
Column 9, line 49, "-2,6dideoxy" should read -- -2,6-dideoxy --.
Column 10, line 2, "1,3,4,5tetrakis" should read -- 1,3,4,5-tetrakis --.

UNITED STATES PATENT AND TRADEMARK OFFICE
CERTIFICATE OF CORRECTION

PATENT NO. : 4,634,765

DATED : January 6, 1987

INVENTOR(S) : Paul S. Liu

It is certified that error appears in the above-identified patent and that said Letters Patent are hereby corrected as shown below:

```
Column 10, line 59, "salt" should read -- (salt) --.
Column 10, line 63, "salt" should read -- (salt) --.
Column 10, line 65, "(1→1)" should read -- (1→7) --.
Column 10, line 67, "4methylbenzenesulfonate salt" should read
-- 4-methylbenzenesulfonate (salt) --.
```

Signed and Sealed this

Nineteenth Day of July, 1988

Attest:

DONALD J. QUIGG

*Attesting Officer*   *Commissioner of Patents and Trademarks*